United States Patent
Stern

(10) Patent No.: US 10,034,693 B2
(45) Date of Patent: Jul. 31, 2018

(54) SPINOUS LAMINAR CLAMP ASSEMBLY

(71) Applicant: Mark S. Stern, La Jolla, CA (US)

(72) Inventor: Mark S. Stern, La Jolla, CA (US)

(*) Notice: Subject to any disclaimer, the term of this patent is extended or adjusted under 35 U.S.C. 154(b) by 0 days.

(21) Appl. No.: 15/643,400

(22) Filed: Jul. 6, 2017

(65) Prior Publication Data

US 2018/0008321 A1    Jan. 11, 2018

Related U.S. Application Data

(60) Provisional application No. 62/359,424, filed on Jul. 7, 2016.

(51) Int. Cl.
*A61B 17/70*  (2006.01)

(52) U.S. Cl.
CPC ...... *A61B 17/7056* (2013.01); *A61B 17/7002* (2013.01); *A61B 17/7047* (2013.01); *A61B 17/7065* (2013.01)

(58) Field of Classification Search
CPC ............ A61B 17/7056; A61B 17/7002; A61B 17/7047; A61B 17/7065
USPC ....... 606/246, 248, 250, 251, 252, 253, 260, 606/264, 270, 276, 277, 278, 324, 330, 606/99, 86 A
See application file for complete search history.

(56) References Cited

U.S. PATENT DOCUMENTS

| | | |
|---|---|---|
| 4,085,744 A | 4/1978 | Lewis |
| 4,269,187 A | 5/1981 | Keene |
| 4,361,141 A | 11/1982 | Tanner |
| 4,382,438 A | 5/1983 | Jacobs |
| 4,409,968 A | 10/1983 | Drummond |
| 4,411,259 A | 10/1983 | Drummond |
| 4,422,491 A | 12/1983 | Cusick, III |
| 4,433,676 A | 2/1984 | Bobechko |
| 4,573,454 A | 3/1986 | Hoffman |
| 4,653,481 A | 3/1987 | Howland |
| 4,686,970 A | 8/1987 | Dove et al. |
| 4,697,582 A | 10/1987 | Peze |
| 4,738,251 A | 4/1988 | Plaza |
| 4,773,402 A | 9/1988 | Asher et al. |
| 4,790,303 A | 12/1988 | Steffee |
| 4,815,453 A | 3/1989 | Cotrel |
| 4,854,304 A | 8/1989 | Zielke |
| 4,998,936 A | 3/1991 | Mehdian |

(Continued)

FOREIGN PATENT DOCUMENTS

| | | |
|---|---|---|
| DE | 3032237 A1 | 3/1982 |
| EP | 0537598 A2 | 4/1993 |

(Continued)

*Primary Examiner* — Pedro Philogene
*Assistant Examiner* — David C Comstock
(74) *Attorney, Agent, or Firm* — Timothy W. Fitzwilliam

(57) ABSTRACT

A spinous laminar clamp system is disclosed herein. The preferred embodiments are either a three or a four-point fixation system at a particular vertebral level. For example, a two-point adjustable fixation below a vertebrae and a single-point non-adjustable point above the vertebrae exemplifies the three-point fixation. Multiple level and further stabilizing is provided by fixation to subjacent vertebrae above and/or below with a connecting rod providing unitization between levels. Specific designs are applicable to the cervical spine; however, fixation at all levels and regions of the human spine are contemplated.

14 Claims, 11 Drawing Sheets

(56) References Cited

U.S. PATENT DOCUMENTS

| | | |
|---|---|---|
| 5,005,562 A | 4/1991 | Cotrel |
| 5,010,879 A | 4/1991 | Moriya et al. |
| 5,024,213 A | 6/1991 | Asher et al. |
| 5,030,220 A | 7/1991 | Howland |
| 5,074,864 A | 12/1991 | Cozad et al. |
| 5,102,412 A | 4/1992 | Rogozinski |
| 5,116,334 A | 5/1992 | Cozad et al. |
| 5,127,912 A | 7/1992 | Ray |
| 5,181,917 A | 1/1993 | Rogozinski |
| 5,242,446 A | 9/1993 | Steffee et al. |
| 5,261,913 A | 11/1993 | Marnay |
| 5,267,999 A * | 12/1993 | Olerud ............... A61B 17/7047 606/277 |
| 5,300,073 A | 4/1994 | Ray et al. |
| 5,334,203 A | 8/1994 | Wagner |
| 5,360,429 A | 11/1994 | Jeanson et al. |
| 5,380,326 A | 1/1995 | Lin |
| 5,382,248 A | 1/1995 | Jacobson et al. |
| 5,395,370 A | 3/1995 | Muller et al. |
| 5,415,659 A | 5/1995 | Lee et al. |
| 5,439,463 A | 8/1995 | Lin |
| 5,542,946 A | 8/1996 | Logroscino et al. |
| 5,611,800 A | 3/1997 | Davis et al. |
| 5,928,232 A | 7/1999 | Howland et al. |
| 6,117,035 A | 9/2000 | Isshiki et al. |
| 6,197,028 B1 | 3/2001 | Ray et al. |
| 6,458,131 B1 | 10/2002 | Ray |
| 6,602,253 B2 | 8/2003 | Richelsoph |
| 6,709,435 B2 | 3/2004 | Lin |
| 6,719,795 B1 | 4/2004 | Cornwall et al. |
| 6,770,075 B2 | 8/2004 | Howland |
| 6,820,844 B2 | 11/2004 | Tiffen et al. |
| 6,958,066 B2 | 10/2005 | Richelsoph et al. |
| 7,029,474 B2 | 4/2006 | Richelsoph et al. |
| 7,048,736 B2 | 5/2006 | Robinson et al. |
| 7,074,239 B1 | 7/2006 | Cornwall et al. |
| 7,131,972 B2 | 11/2006 | Mazda et al. |
| 7,335,203 B2 | 2/2008 | Winslow et al. |
| 7,338,490 B2 | 3/2008 | Ogilvie et al. |
| 7,458,981 B2 | 12/2008 | Fielding et al. |
| 7,476,254 B2 | 1/2009 | White et al. |
| 7,575,588 B2 | 8/2009 | Barker et al. |
| 7,585,316 B2 | 9/2009 | Trieu |
| 7,588,592 B2 | 9/2009 | Winslow et al. |
| 7,588,951 B2 | 9/2009 | Mangrum et al. |
| 7,591,637 B2 | 9/2009 | Muehlhausen et al. |
| 7,611,526 B2 | 11/2009 | Carl et al. |
| 7,635,377 B2 | 12/2009 | Zucherman et al. |
| 7,648,508 B2 | 1/2010 | Lutz et al. |
| 7,658,753 B2 | 2/2010 | Carl et al. |
| 7,662,187 B2 | 2/2010 | Zucherman et al. |
| 7,666,208 B1 | 2/2010 | Asfora |
| 7,666,209 B2 | 2/2010 | Zucherman et al. |
| 7,670,358 B2 | 3/2010 | Barry |
| 7,670,383 B1 | 3/2010 | Brown et al. |
| 7,682,376 B2 | 3/2010 | Trieu |
| 7,686,809 B2 | 3/2010 | Triplett et al. |
| 7,691,130 B2 | 4/2010 | Bruneau et al. |
| 7,708,765 B2 | 5/2010 | Carl et al. |
| 7,722,678 B2 | 5/2010 | Brown et al. |
| 7,727,233 B2 | 6/2010 | Blackwell et al. |
| 7,749,253 B2 | 7/2010 | Zucherman et al. |
| 7,763,073 B2 | 7/2010 | Hawkins et al. |
| 7,763,074 B2 | 7/2010 | Altarac et al. |
| 7,766,940 B2 | 8/2010 | Kwak et al. |
| 7,776,069 B2 | 8/2010 | Taylor |
| 7,776,072 B2 | 8/2010 | Barry |
| 7,780,709 B2 | 8/2010 | Bruneau et al. |
| 7,789,898 B2 | 9/2010 | Peterman |
| 7,799,054 B2 | 9/2010 | Kwak et al. |
| 7,799,058 B2 | 9/2010 | Froehlich et al. |
| 7,806,911 B2 | 10/2010 | Peckham |
| 7,833,246 B2 | 11/2010 | Mitchell |
| 7,837,711 B2 | 11/2010 | Bruneau et al. |
| 7,842,071 B2 | 11/2010 | Hawkes |
| 7,846,185 B2 | 12/2010 | Carls et al. |
| 7,862,590 B2 | 1/2011 | Lim et al. |
| 7,862,591 B2 | 1/2011 | Dewey et al. |
| 7,896,906 B2 | 3/2011 | Kwak et al. |
| 7,922,750 B2 | 4/2011 | Trautwein et al. |
| 7,927,354 B2 | 4/2011 | Edidin et al. |
| 7,927,355 B2 | 4/2011 | Berrevoets et al. |
| 7,985,244 B2 | 7/2011 | Borgstrom et al. |
| 7,985,246 B2 | 7/2011 | Trieu |
| 7,993,342 B2 | 8/2011 | Malandain et al. |
| 7,998,208 B2 | 8/2011 | Kohm et al. |
| 8,002,801 B2 | 8/2011 | Carl et al. |
| 8,012,207 B2 | 9/2011 | Kim |
| 8,016,860 B2 | 9/2011 | Carl et al. |
| 8,029,541 B2 | 10/2011 | Alamin et al. |
| 8,029,542 B2 | 10/2011 | Zucherman et al. |
| 8,029,549 B2 | 10/2011 | Malandain et al. |
| 8,029,550 B2 | 10/2011 | Dewey et al. |
| 8,043,335 B2 | 10/2011 | Malandain et al. |
| 8,043,336 B2 | 10/2011 | Taylor |
| 8,043,337 B2 * | 10/2011 | Klyce ............... A61B 17/7047 606/252 |
| 8,043,338 B2 | 10/2011 | Dant |
| 8,043,345 B2 | 10/2011 | Carl et al. |
| 8,048,166 B2 | 11/2011 | Brown et al. |
| 8,062,337 B2 | 11/2011 | Bruneau et al. |
| 8,066,742 B2 | 11/2011 | Anderson et al. |
| 8,070,779 B2 | 12/2011 | Khoo |
| 8,070,783 B2 | 12/2011 | Kwak et al. |
| 8,092,459 B2 | 1/2012 | Malandain |
| 8,092,496 B2 | 1/2012 | Kwak et al. |
| 8,092,535 B2 | 1/2012 | Zucherman et al. |
| 8,096,995 B2 | 1/2012 | Kohm et al. |
| 8,097,019 B2 | 1/2012 | Mitchell et al. |
| 8,105,357 B2 | 1/2012 | Bruneau et al. |
| 8,105,363 B2 | 1/2012 | Fielding et al. |
| 8,114,135 B2 | 2/2012 | Malandain |
| 8,123,752 B2 | 2/2012 | Zucherman et al. |
| 8,123,782 B2 | 2/2012 | Altarac et al. |
| 8,123,807 B2 | 2/2012 | Kim |
| 8,128,659 B2 | 3/2012 | Ginsberg |
| 8,128,661 B2 | 3/2012 | Zucherman et al. |
| 8,128,662 B2 | 3/2012 | Altarac et al. |
| 8,147,517 B2 | 4/2012 | Trieu et al. |
| 8,152,837 B2 | 4/2012 | Altarac et al. |
| 8,157,840 B2 | 4/2012 | Zucherman et al. |
| 8,162,982 B2 | 4/2012 | Alamin et al. |
| 8,167,944 B2 | 5/2012 | Kim |
| 8,187,305 B2 | 5/2012 | Malandain et al. |
| 8,187,307 B2 | 5/2012 | Alamin et al. |
| 8,216,275 B2 | 7/2012 | Fielding et al. |
| 8,216,276 B2 | 7/2012 | Trieu |
| 8,221,463 B2 | 7/2012 | Zucherman et al. |
| 8,221,465 B2 | 7/2012 | Trieu et al. |
| 8,235,265 B2 | 8/2012 | Barnes |
| 8,240,528 B2 | 8/2012 | Barnes |
| 8,246,658 B2 | 8/2012 | Rezach |
| 8,252,029 B2 | 8/2012 | Morancy-Meister et al. |
| 8,252,031 B2 | 8/2012 | Carls et al. |
| 8,262,697 B2 | 9/2012 | Kirschman |
| 8,273,107 B2 | 9/2012 | Zucherman et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,308,767 B2 | 11/2012 | Hochschuler et al. |
| 8,308,771 B2 | 11/2012 | Bennett et al. |
| 8,317,864 B2 | 11/2012 | Kim |
| 8,328,848 B2 | 12/2012 | Lowery et al. |
| 8,343,190 B1 | 1/2013 | Mueller et al. |
| 8,348,976 B2 | 1/2013 | Kohm et al. |
| 8,348,977 B2 | 1/2013 | Bruneau et al. |
| 8,348,978 B2 | 1/2013 | Trieu et al. |
| 8,403,961 B2 | 3/2013 | Fielding et al. |
| 8,403,964 B2 | 3/2013 | Fielding et al. |
| 8,409,282 B2 | 4/2013 | Kim |
| 8,425,559 B2 | 4/2013 | Tebbe et al. |
| 8,454,659 B2 | 6/2013 | Zucherman et al. |
| 8,454,660 B2 | 6/2013 | Alamin et al. |
| 8,455,525 B2 | 6/2013 | Miller |

(56) References Cited

U.S. PATENT DOCUMENTS

| | | | |
|---|---|---|---|
| 8,470,000 B2 | 6/2013 | Trautwein et al. | |
| 8,486,110 B2 | 7/2013 | Fielding et al. | |
| 8,523,904 B2 | 9/2013 | Alamin et al. | |
| 8,529,606 B2 | 9/2013 | Alamin et al. | |
| 8,529,607 B2 | 9/2013 | Alamin et al. | |
| 8,545,500 B2 | 10/2013 | Babat et al. | |
| 8,562,650 B2 | 10/2013 | Dace | |
| 8,562,653 B2 | 10/2013 | Alamin et al. | |
| 8,568,453 B2 | 10/2013 | Addou | |
| 8,568,460 B2 | 10/2013 | Zucherman et al. | |
| 8,574,267 B2 | 11/2013 | Linares | |
| 8,613,747 B2 | 12/2013 | Altarac et al. | |
| 8,628,574 B2 | 1/2014 | Altarac et al. | |
| 8,668,719 B2 | 3/2014 | Alamin et al. | |
| 8,672,974 B2 | 3/2014 | Zucherman et al. | |
| 8,672,975 B2 | 3/2014 | Zucherman et al. | |
| 8,672,976 B2 | 3/2014 | Kilpela et al. | |
| 8,690,918 B1 | 4/2014 | Williams | |
| 8,696,710 B2 | 4/2014 | Fielding et al. | |
| 8,709,043 B2 | 4/2014 | Kwak et al. | |
| 8,740,941 B2 | 6/2014 | Thramann | |
| 8,740,948 B2 | 6/2014 | Reglos et al. | |
| 8,767,460 B2 | 7/2014 | Matsunami | |
| 8,771,277 B2 | 7/2014 | Zappacosta et al. | |
| 8,771,418 B2 | 7/2014 | Je et al. | |
| 8,790,372 B2 | 7/2014 | Alamin et al. | |
| 8,801,757 B2 | 8/2014 | Abdou | |
| 8,828,070 B2 | 9/2014 | Romoda et al. | |
| 8,840,646 B2 | 9/2014 | Vittur et al. | |
| 8,845,697 B2 | 9/2014 | Montello et al. | |
| 8,845,726 B2 | 9/2014 | Tebbe et al. | |
| 8,864,828 B2 | 10/2014 | Altarac et al. | |
| 8,876,866 B2 | 11/2014 | Zappacosta et al. | |
| 8,882,805 B1 | 11/2014 | Maccree | |
| 8,888,816 B2 | 11/2014 | Zucherman et al. | |
| 8,894,686 B2 | 11/2014 | Zucherman et al. | |
| 8,900,271 B2 | 12/2014 | Kim | |
| 8,911,476 B2 | 12/2014 | Schmierer et al. | |
| 8,915,970 B2 | 12/2014 | Porter et al. | |
| 8,932,333 B2 | 1/2015 | Kirschman | |
| 8,940,019 B2 | 1/2015 | Gordon et al. | |
| 8,945,183 B2 | 2/2015 | Altarac et al. | |
| 8,961,564 B2 | 2/2015 | Gordon et al. | |
| 9,011,491 B2 | 4/2015 | Carl et al. | |
| 9,011,493 B2 | 4/2015 | Zappacosta et al. | |
| 9,023,084 B2 | 5/2015 | Kim | |
| 9,039,742 B2 | 5/2015 | Altarac et al. | |
| 9,060,810 B2 | 6/2015 | Kercher et al. | |
| 9,060,813 B1 | 6/2015 | Uribe | |
| 9,060,816 B2 | 6/2015 | Abdou | |
| 9,095,380 B2 | 8/2015 | Mir | |
| 2003/0032959 A1* | 2/2003 | Yeh | A61B 17/7001 606/261 |
| 2003/0187435 A1* | 10/2003 | Lin | A61B 17/7001 606/250 |
| 2004/0097931 A1 | 5/2004 | Mitchell | |
| 2004/0153071 A1 | 8/2004 | Zucherman et al. | |
| 2004/0167520 A1 | 8/2004 | Zucherman et al. | |
| 2004/0220568 A1 | 11/2004 | Zucherman et al. | |
| 2004/0249379 A1 | 12/2004 | Winslow | |
| 2005/0075634 A1 | 4/2005 | Lucherman | |
| 2005/0203512 A1 | 9/2005 | Hawkins et al. | |
| 2005/0216017 A1 | 9/2005 | Fielding | |
| 2006/0229607 A1 | 10/2006 | Brumfield | |
| 2011/0264211 A1 | 10/2011 | Benz et al. | |
| 2012/0078304 A1* | 3/2012 | Jensen | A61B 17/7071 606/251 |
| 2012/0109204 A1 | 5/2012 | Linares | |
| 2012/0109209 A1 | 5/2012 | Rezach | |
| 2012/0150228 A1 | 6/2012 | Zappacosta | |
| 2012/0296379 A1 | 11/2012 | Morancy-Meister et al. | |
| 2013/0090688 A1 | 4/2013 | Montello | |
| 2014/0107703 A1 | 4/2014 | Smisson, III et al. | |
| 2014/0207199 A1 | 7/2014 | Gordon et al. | |
| 2014/0288606 A1 | 9/2014 | Pagano | |
| 2014/0343612 A1 | 11/2014 | Rezach et al. | |
| 2017/0112538 A1* | 4/2017 | McCarthy | A61B 17/707 |
| 2017/0303970 A1* | 10/2017 | Puryear | A61B 17/7032 |

FOREIGN PATENT DOCUMENTS

| | | | |
|---|---|---|---|
| FR | 2743491 B1 | 7/1998 | |
| FR | 2849590 B1 | 3/2005 | |
| WO | 2003026521 A1 | 4/2003 | |
| WO | 2005041792 A1 | 5/2005 | |
| WO | 2006110578 A2 | 10/2006 | |
| WO | 2007052975 A1 | 5/2007 | |
| WO | 2008051423 A1 | 5/2008 | |
| WO | 2008051801 A2 | 5/2008 | |
| WO | 2008051802 A2 | 5/2008 | |
| WO | 2009127041 A1 | 10/2009 | |
| WO | 2009149407 A1 | 12/2009 | |
| WO | 2009149414 A1 | 8/2010 | |
| WO | 2010088621 A1 | 8/2010 | |
| WO | 2010010975 A1 | 9/2010 | |
| WO | 2010121256 A1 | 10/2010 | |
| WO | 2011017363 A1 | 2/2011 | |
| WO | 2011031924 A2 | 3/2011 | |

* cited by examiner

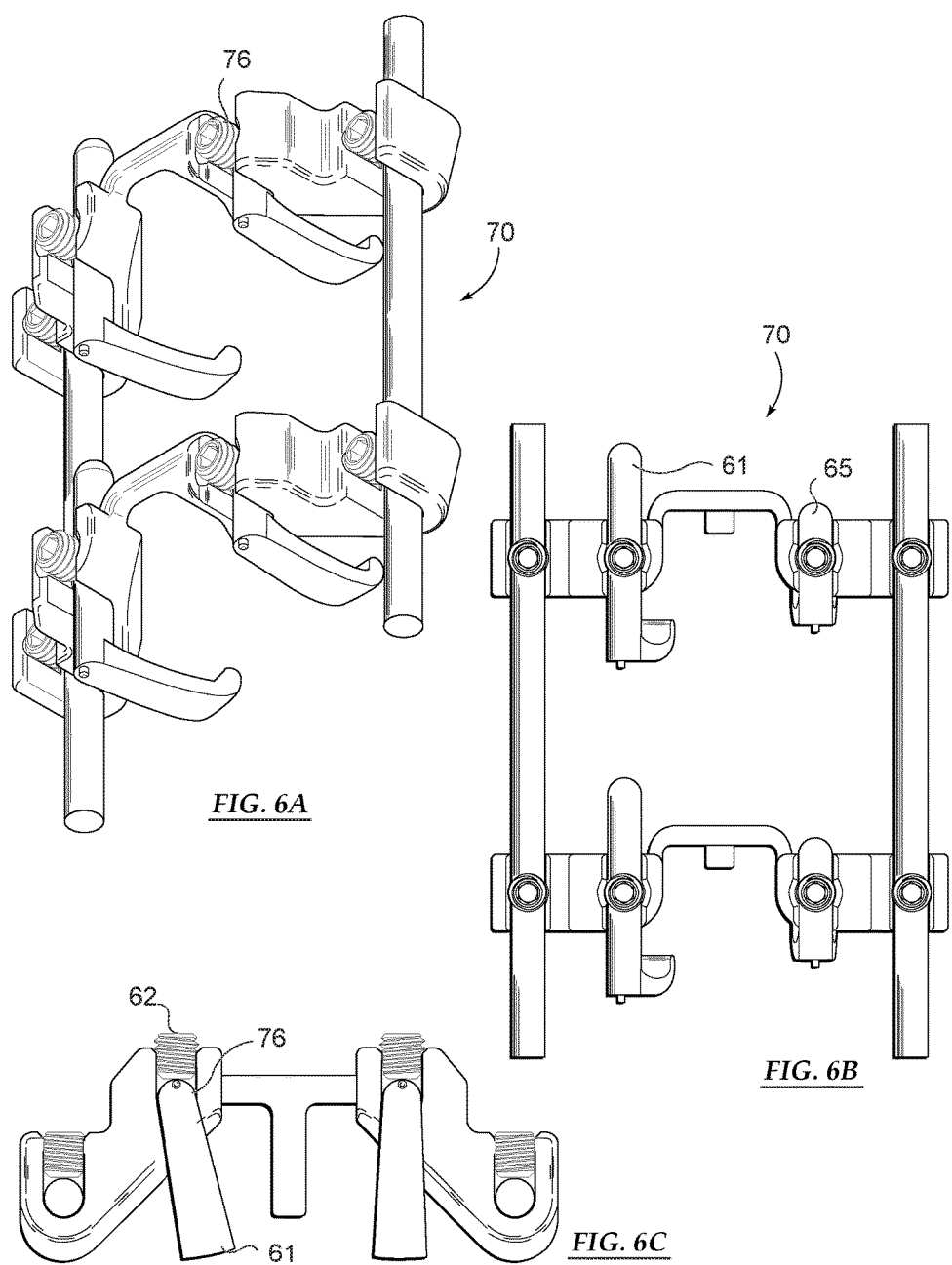

SPINOUS LAMINAR CLAMP ASSEMBLY

PRIORITY CLAIM

This patent application claims benefit of the priority date of U.S. Prov. Pat. App. Ser. No. 62/359,424 filed on Jul. 7, 2016 entitled "Spinous Laminar Clamp System and Method of Insertion." Accordingly, the entire contents this U.S. provisional patent submission is hereby expressly incorporated by reference.

BACKGROUND OF THE INVENTION

Field of the Invention

The present invention pertains generally to devices surgically implanted for spinal stabilization. More specifically, the present invention relates to clamp devices together with an insertion tool for cervical spine fixation in the management of vertebral fractures.

Description of the Prior Art

Systems and methods for spinal stabilization and fixation particularly to treat fractures thereof have been introduced heretofore. A sub-specialization herein is the treatment and healing of the Type-II Odontoid Fracture occurring on the dens portion of the cervical spine. With regard to FIG. 1A and FIG. 1B, the odontoid process, a.k.a. dens, is a peg-like protrusion shown on the uppermost part of the spine corresponding to the C2 vertebrae. This type of injury is very common in accidents involving elderly population wherein the upper cervical (C0-C2) is the most common fracture location in patients 65 years of age and above. In addition to trauma event, elderly persons are particularly susceptible to falling with an extension event, hitting of the head against a cupboard, sink or wall causing fracturing at the base of the dens. The frequent occurrence of this fracture has increased recently as people live longer reaching an age where falls are more common.

Other fractures (e.g. Type-1 and Type-III) specifically involving the C1-C2 vertebrae are also pertinent to devices and methods herein. More particularly, the Type-I Odontoid fracture would occur at the top portion of the dens and is generally stable without the need for surgery. The Type-II, as stated, is the most common of the three and occurs at the base of the dens where it protrudes from the body of the C2. The Type-III occurs just below the base of the dens at the thicker vertebral C2 body. The Type-III fracture prognosis would call for better healing on thicker, more stable area with better blood supply thereto.

There remains some debate as to the proper management or Type II fractures, particularly in the elderly wherein prolonged cervical immobilization is weighed against the risks of surgical intervention. These patients have a high degree of failure of fusion and proper bone healing. And, existing technologies have a significant morbidity and mortality. More specifically, a least invasive alternative is the halo orthosis device that is essentially a head and neck brace that does not require pin-insertion-into-the-spine type surgery to implement. Instead, a metal ring is attached to a patient's skull which is subsequently attached to a vest. But however, the success rate for the halo device is small. This orthosis is poorly tolerated by elderly patients with low yield for fusion and high complication rate of infection, further falls, and other complications.

A second option is the anterior dens screws that require mobilizing the esophagus and trachea from an anterior approach with a high degree of complication of esophageal injury, swallowing disorder, and aspiration pneumonia. Also, the success rate for drills and screws is small due to poor access, and inadequate stabilization; and it is not tolerated in the age group that experiences most frequently dens fractures.

Another option is the Harms pedicle also employing screws, which, in this instance require significant immobilization of vascular and neutral structures of the C1-C2 junction increasing risk of bleeding, nerve injury, damaged veins and perforation of the vertebral artery as the screw enters the bone and possibly displace either medially into the spinal cord or laterally into the vertebral arteries. Hence transarticular screws will liking produce excessive bleeding and complications and also initially require a lateral aspect x-ray.

Yet an additional technique has been termed the Brooks technique which involves wires and screws together. Wiring the C1 to the C2 unfortunately has a low yield for fusion with concern that the wires can dislodge and, therefore, fail at immobilization. In sum, all of these previous devices and methods have risks, complications, an/or other inherent failures.

More recent alternative examples surgical devices and techniques are gradually being introduced. A pair of pertinent examples are introduced by Howland et al., U.S. Pat. No. 5,928,232, entitled "Spinal Fixation System," and by Pagano, U.S. Pub. Pat. App. No. 2014/0288606, entitled "Odontoid Fracture Dynamic Compression Apparatus and Method." Howland et al. identify the lamina and the spinous process as the strong sections of vertebra most appropriate for attachment of the fixation device.

These devices and techniques may yield some successes, but however further variations and improvements are desired in the area of spinal fixation and are disclosed herein. For example, a solution is needed with greater safety and reduced risk than that of pedicel screws that may be added only when needed, and can be easily adaptable to cervical, thoracic and lumbar vertebra. Accordingly, the present invention introduces a fixation device attaching to the thin laminar plates (lamina) consisting of layers bone membranes.

In light of the above, it is an object of the present to provide an autonomous laminar clamp solution; and further specifically provide a three-point or four-point clamp system particular to a vertebral level with a second set of three-point or four-point clamps offset. Angular offset approach to the specific laminae can be achieved by rotating clamps and/or a single clamp system may be employed, or as further detailed here. It is additionally an object of the present invention to provide a fixation solution specifically to manage the Type II Odontoid Fracture, but other fractures as well, such as Type I and Type III, the Jefferson Fracture, and other cervical, thoracic and lumbar spine fractures. Still further, by change clamp size and shape, the present invention seeks to provide solutions applicable to the cervical 1 to the cervical 7, from thoracic 1 to thoracic 12, and from lumbar 1 to lumbar 5. Yet further, it is an object of the present invention to provide a solution addressing vertebral malalignment and frank subluxation. Still further, it is an object of the present invention to provide a solution with all components with biocompatible material to the vertebrae, providing strength and longevity until fusion and healing occurs. It is still further an object to provide alternative approaches depending on type and location of fracture and therefore pathology dependent. Additionally further, it is an object of the present invention to provide a device the can be easily removed, if necessary, at a later date should complications arise such as infection, or complication requiring additional surgery. It is yet still further an object of the present invention to provide a clamp system appropriate for affixing to complex geometries and irregular surfaces.

BRIEF SUMMARY OF THE INVENTION

The present invention specifically addresses and alleviates the above mentioned deficiencies, more specifically, the present invention, in a first aspect, is a spinous laminar clamp for fixating and unitizing a human spine comprising: a first base portion providing structural integrity thereto; and a first slot through a top and a bottom of the first base portion for receiving a first lower caudal hook, wherein the first lower caudal hook is slidingly adjustable vertically via the first slot. The invention in this first aspect is additionally characterized in that an upper cephalad hook is configured to the first base portion, the upper cephalad hook and the lower caudal hook together for tightening to a vertebral surface (for example, a laminar surface) for fixating and unitizing the human spine.

The invention in the first aspect is additionally characterized wherein the first slot is through the top and the bottom of the first base portion and it further comprises an opening to a rear of the first base portion, the opening providing a "U" channel in the top aspect, the opening configured to slidingly receive a stem of the first lower caudal hook in its upright position thereby providing for a rear loading of the first caudal hook, further thereby the stem of the first lower caudal hook is able to slide laterally in its upright position for surgical placement and subsequently can slide up and down in its upright position via the first slot. The opening further comprises threads; and the threads are configured to receive a tightening screw through the rear of the first base portion for contacting the stem of the first lower caudal hook. Still further, the threads are configured partially hemispherically through opposing walls of the first slot.

The spinous laminar clamp for fixating and unitizing vertebrae in this aspect is additionally characterized in that the tightening screw comprises a bead at an end thereof for optimally contacting and securing the stem of the first lower caudal hook. Also, the invention is further defined wherein the first lower caudal hook comprises a stem, the stem being cylindrical in shape, the cylindrical shape providing rotation of the stem within the first slot, the rotation for aligning to a complex geometry of the vertebral surface.

The invention in this aspect is further characterized as comprising: a second base portion in a common horizontal plane with said first base portion; and a second slot through a top and a bottom of the second base portion for receiving a second lower caudal hook, wherein the second lower caudal hook together with the first cephalad hook and first lower caudal hook are for fixating and unitizing a human spine, wherein thereby the first and the second caudal hooks together with the first cephalad hook provide a three-point fixation to the spine, the three-point fixation being particular to a single vertebral level.

The spinous laminar clamp herein further comprises a bridge connecting the first and second base portions, the bridge being an isthmus between the first and the second base portions, wherein the bridge comprises said first cephalad hook at a center thereof, thereby the first cephalad hook is configured to the first base portion via said bridge, wherein the first and second base portions together form a first collective base on the common horizontal plane providing structural integrity to the spinous laminar clamp.

Still further, in invention in the first aspect is characterized as comprising: an arm extending forward from the bridge, the arm having a curved portion at an end thereof; and a spike configured to the curved portion for fixedly contacting the vertebral surface. Yet another third slot is also provided through a top and a bottom of the first base portion for receiving a first connecting rod, the third slot at an outer portion of the first base portion with respect to the first slot, wherein the first connecting rod is configured to a third base portion. The third base portion has fixation at a vertebral level directly above or below (subjacent) a vertebral level of the first and second base portion, thereby providing fixation at two vertebral levels.

In still a second aspect, the invention may be characterized as spinous laminar clamp comprising: a first base portion providing structural integrity thereto; a first aperture through a top and a bottom of the first base portion for slidingly receiving an upper cephalad hook; and a fixed lower jaw coupled to the first base portion opposite the cephalad hook, the cephalad hook and the lower jaw together for tightening to a vertebral surface (for example, a laminar surface).

Further in the second aspect, the invention may be characterized wherein the fixed lower jaw comprises a hole therethrough to receive the cephalad hook stem. The spinous laminar clamp further comprises a threaded aperture through a side of the first base portion configured with a tightening screw for tightening to the cephalad hook stem via the threaded aperture. The lower jaw further comprises a spike for fixating and unitizing, further wherein the lower jaw and the cephalad hook together form an underbite (when in lowest position but also when not in use) thereby wherein the lower jaw protrudes slightly farther than the upper hook.

Additionally in the second aspect, the invention may be characterized as comprising: a second base portion in a same horizontal plane with said first base portion; a second fixed lower jaw configured at an underside of the second base portion; and a second aperture through a top and a bottom of the second base portion for receiving a second cephalad hook. The second fixed lower jaw together with the first cephalad hook and first fixed lower jaw are for fixating and unitizing a human spine. Additionally thereby, the first and second cephalad hook together with the first and second fixed lower jaw provide a four-point fixation to the spine, four-point fixation being particular to a single vertebral level. Also in the second aspect the invention is characterized as having an isthmus connecting the first and second base portion, the isthmus providing an approximately 90 degree offset with respect to the first and second base portions thereby providing the offset to the first and second cephalad hooks.

In still a third aspect, the invention may be characterized as a spinous laminar clamp assembly providing fixation at multiple vertebral levels comprising a first base portion configured to a first hook with a first stem slidingly received by the first base portion; a second base portion configured to a second hook with a second stem slidingly received by the second base portion, the second base portion in a first shared horizontal plane to the first base portion; a first isthmus between the first and the second base portion, the first isthmus having a third hook, wherein the first hook, second hook and third hook provide a three-point fixation to a first vertebral level; a third and a fourth base portion configured subjacent (below) said first and said second base portions, the third and fourth base portion in a second horizontal plane further fixated to a second vertebral level; and a connecting rod coupling the first and second base portions to the third and the fourth base portions, the first, the second, the third and the fourth base portions together with the connecting rod providing fixation at the multiple vertebral levels.

The spinous laminar clamp assembly in the third aspect is additionally characterized as further comprising an insertion instrument having an upper and a lower jaw at a distal end for grasping and tightening the first hook and the second hook to a vertebral surface. Further, the first, the second, the third, and the fourth base portions each further comprise a slot through a top and a bottom. Each slot is U-shaped in a top aspect wherein a pair of opposing side walls of the slot are threaded, forming a threaded side channel out of a rear of each of the first, the second, and the third base portions for tightening and securing the connecting rod which is a vertical connecting rod for connecting the multiple levels.

These, as well as other advantages of the present invention, will be more apparent from the following description and drawings. It is understood that changes in the specific structure shown and described may be made within the scope of the claims, without departing from the spirit of the invention.

While the apparatus and method has or will be described for the sake of grammatical fluidity with functional explanations, it is to be expressly understood that the claims, unless expressly formulated under 35 USC § 112, or similar applicable law, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC § 112 are to be accorded full statutory equivalents under 35 USC § 112, or similar applicable law. The invention can be better visualized by turning now to the following drawings wherein like elements are referenced by like numerals.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 6A is a perspective view of yet a third preferred embodiment identical to the second preferred embodiment in most respects;

FIG. 6B is an elevation view thereof; and

FIG. 6C is finally a top plan view thereof.

DESCRIPTION OF PREFERRED EMBODIMENTS

Figure 1A:
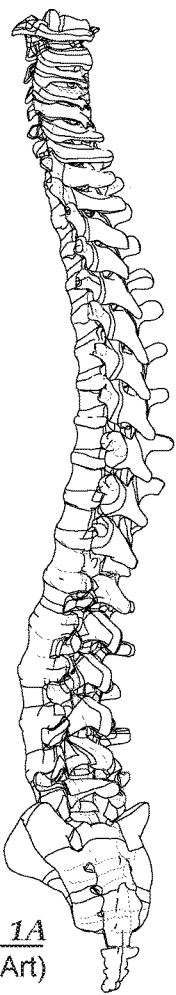
FIG. 1A and FIG. 1B illustrate perspective views of an exemplary human spine.
Figure 1B:
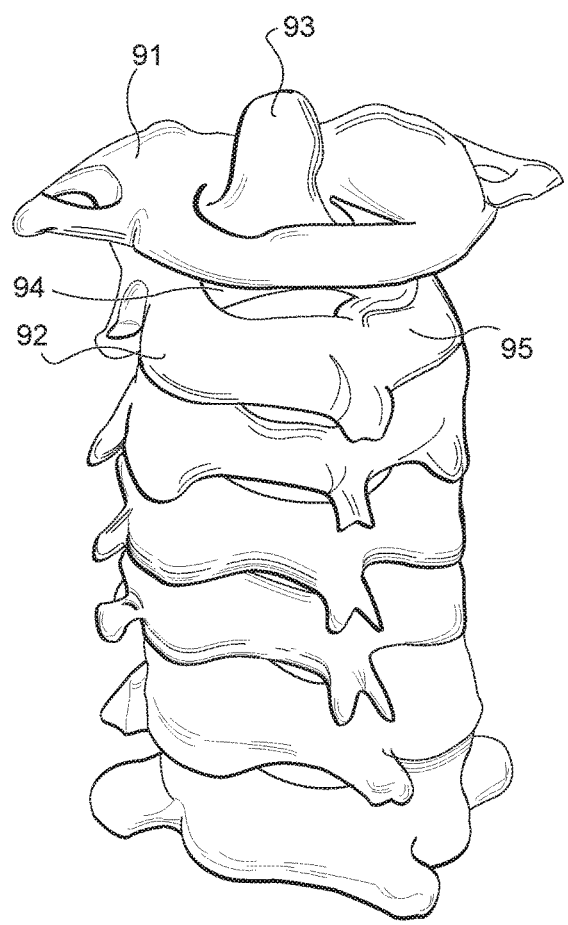

Referring initially FIG. 1A and FIG. 1B a human spine 99 is shown in perspective views. Again, by way of background, an upper area of the cervical spine 99 is emphasized at the (C1) 91 and the (C2) 92 levels. A Type II fracture will occur at the base of the dens 93, a.k.a. odontoid process. A Type III fracture occurs just below the base of the dens 93 at the thicker area 94. The posterior laminar surface 95 is relatively better suited for spinal fixation as compared to lateral portions of the spine due to healing properties following surgery and reduced blood loss during the surgical implant procedure. Its 95 unique structure is also better suited for stabilization comprising bone membrane in layers ultimately forming a thing plate providing some space for access. The basic components of the spinal laminar clamp assemblies 10, 50, 70 are not only intended for cervical levels (C1) to (C7) of the spine, but are further adaptable to all levels, including the lumbar and thoracic regions of the spine. As such, by varying size of hooks 21, 31, 59, 61, 65, adjusting the curvature of said hooks 21, 31, 59, 61, 65, and other modifications, the clamp assemblies 10, 50, 70 and combinations thereof, can be adaptable to all areas of the spine. It should be noted that applicable surgical techniques may be slightly varied for pathology and fracture area.

Figure 2A:
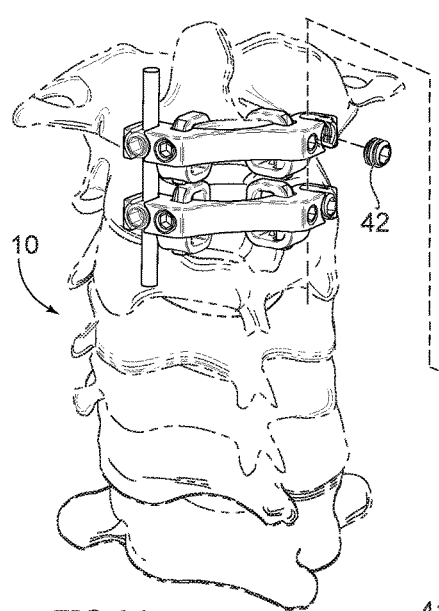
FIG. 2A is a partially assembled, partially exploded view of a first preferred lamina fixation device of the present invention.
Figure 2B:
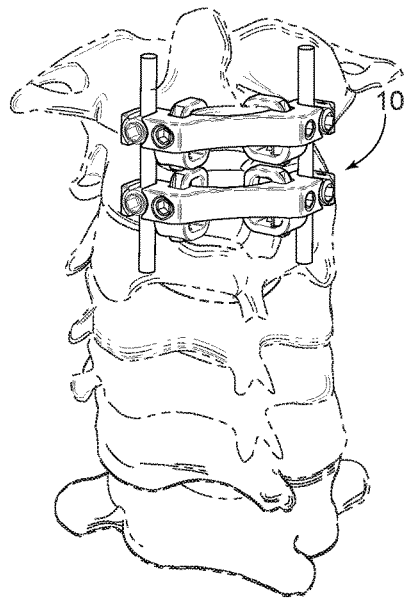
FIG. 2B is an isometric view of the device positioned and in use.
Figure 2C:
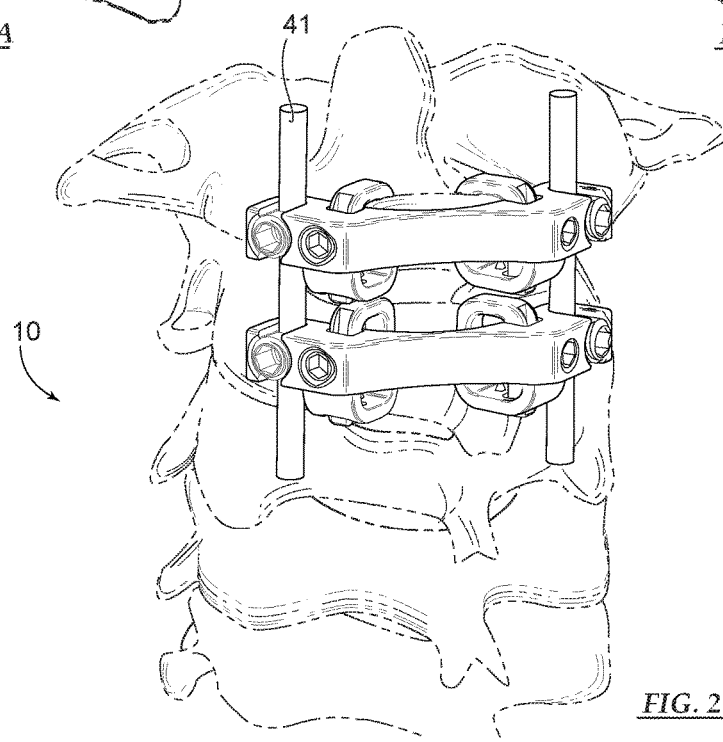
FIG. 2C is an enlarged view thereof.
Figure 3A:
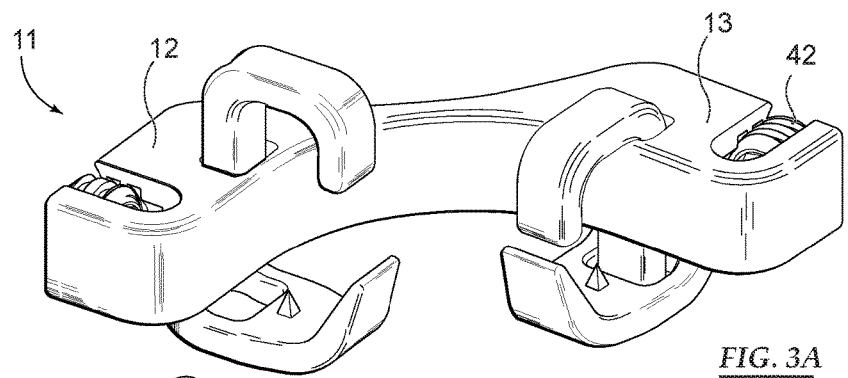
FIG. 3A is an additional enlarged isometric view of the first preferred device from a forward vantage point.

With regard to FIG. 2A and FIG. 3A, a first preferred partially assembled spinous laminar clamp assembly has two laminar clamp base portions 12, 13 (FIG. 3A), that are side by side. An additional set of base portions 12, 13 are set below subjacent to secure two cervical levels 91, 92. Also with regard to FIG. 2B and FIG. 2C, vertical rods 41 connect the base portions 12, 13 each at multiple levels. The two base portions 12, 13 at the same level form a collective base 11 connected by an isthmus 14 that provides a 90 degrees offset. Further the clamps connect at a posterior of the vertebrae at the left and right lamina 95. FIG. 2B provides an isometric view of the first preferred embodiment 10 positioned and in use; meanwhile FIG. 2C provide an enlarged view of the spinous laminar clamp assembly 10 providing grasping, tightening, fixating and unitizing a spine. The basic components of the invention are the base portions 12, 13, 52, 53 that form collective bases 11, 51 or vertebral units and their associated hooks/fixed jaws 21, 31, 59, 61, 65 for fixation, fusion fracture healing, and/or correction of deformity, correction of previously performed surgery, misalignment due to injury, posture, or genetics, tumors, and subluxations.

Figure 2D:
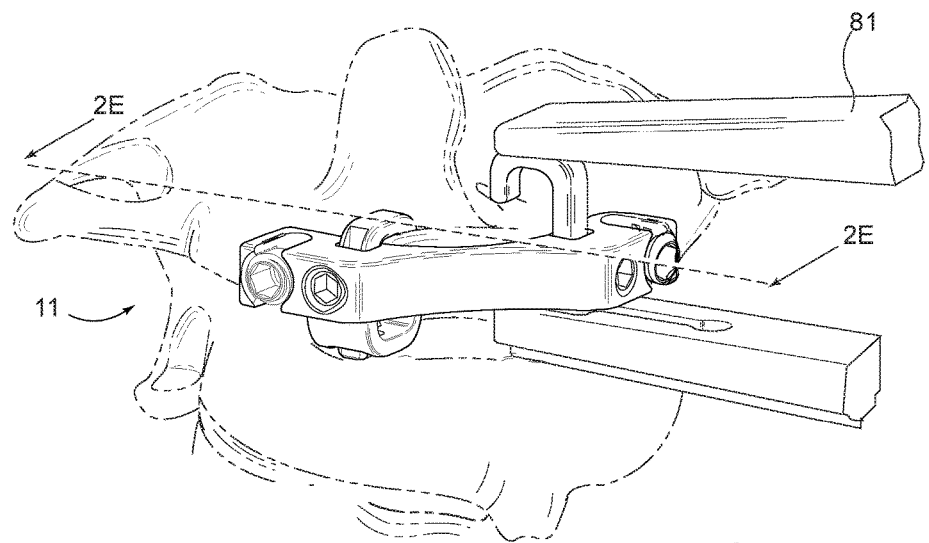
FIG. 2D is still further an enlarged view at a single vertebral level and an exemplary insertion device.
Figure 2E:
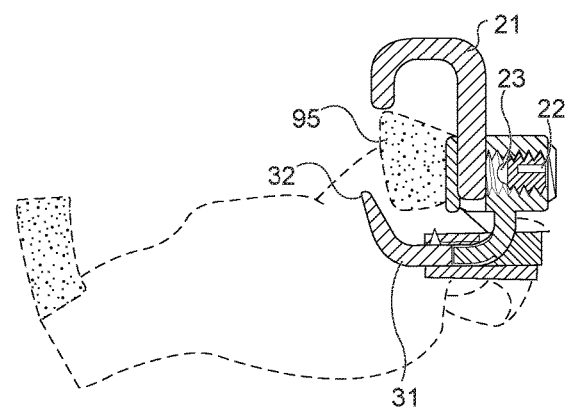
FIG. 2E a cross-sectional view taken along line 2E-2E in FIG. 2D.
Figure 2F:
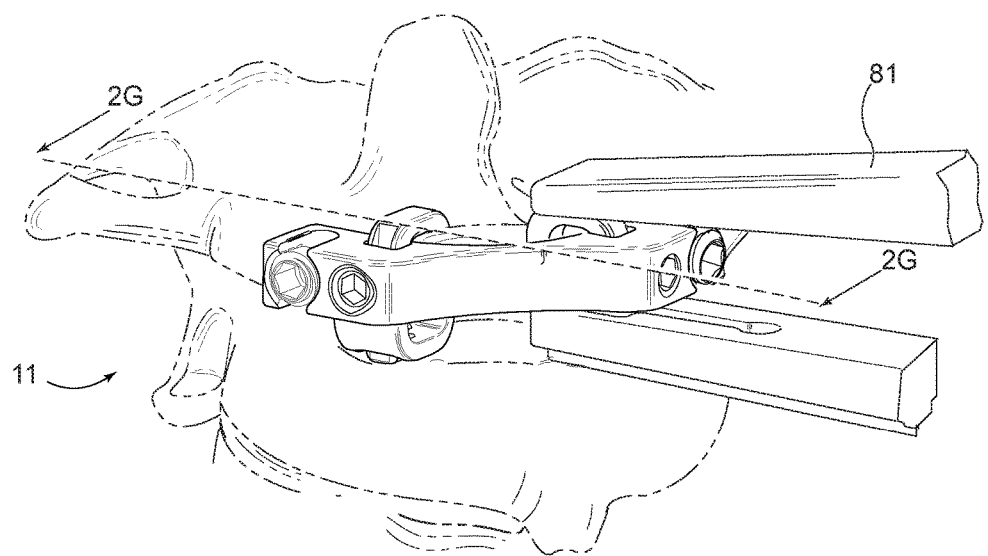
FIG. 2F is still further an enlarged view at a single vertebral level showing the device being cinched down on a laminar surface.

FIG. 2D provides an additional enlarged view of the first preferred embodiment 10 at a single vertebral level 91 to include an exemplary insertion device 81. The insertion instrument 81 may be in the form of thongs, elongated forceps, or cinching and clamping jaws that enclose from above and below as clearly shown in FIG. 2E, FIG. 2F, and FIG. 2G.

Regarding FIG. 2A through FIG. 2G, the invention in another aspect is a spinous laminar clamp assembly 10 having two sets of two base portions 12, 13. Further in this aspect the invention is a spinal fixation system 10 that includes an insertion instrument 81. As shown, an insertion instrument 81 is provided for cinching down on each hook 21 and jaw 31 combination. The insertion instrument 81 further comprises opposing arms connected in a center by a scissor joint coupling and providing relative movement of each arm. The insertion instrument also has similar construction and mechanical advantage as pliers or forceps. Also in a preferred embodiment, an elongated Allen wrench type tool with a tee handle at a proximal end thereof for tightening the torque screw 22 and the locking screw 42.

Also in a preferred surgical method, the upper and lower clamp assemblies 11 are positioned; and then they are serially pinched with the insertion instrument 81, further successive torque screws 22 are tightened; and the locking screws 42 are tightened for fixing and unitizing. It is additionally contemplated herein that insertion instrument can be ratcheted or measured shut to gradually, carefully and reversibly close hooks 21, 31, 59, 61, 65 in all embodiments 10, 50 70 contemplated herein. Further, the clamping mechanism can be loosened, if necessary, for further placement if there is malalignment or need for removal for various events such as infection.

Figure 2G:
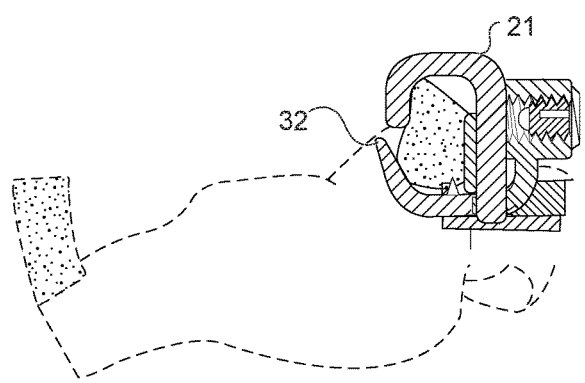
FIG. 2G an cross-sectional view taken along line 2G-2G in FIG. 2F.

FIG. 2G best illustrates the fixation with the lower jaw spike 34 and upper hook 21 portion connecting around the caudal lamina 95. Additionally with regard to FIG. 2G, the lower jaw 31 and the cephalad hook 21 together form an underbite (when in lowest position but also when not in use) thereby wherein the lower jaw 31 protrudes slightly farther than the upper hook 21.

FIG. 3A provides an additional enlarged isometric view of the laminar clamp 10 from a forward vantage point. As stated, first and second base portions 12, 13 are offset by approximately 90 degrees. Each 12, 13 has an aperture 15 through a top and a bottom for slidingly receiving an upper cephalad hook 21 that forms an upper part of each clamp 10 collective base portion 11. A fixed lower jaw 31 coupled to each base portion 12, 13 at the base opposite the cephalad hook. Additionally, the cephalad hook 21 and the lower jaw 31 are tightened together and to the lamina 95. As stated, the fixed lower jaw 31 is at the caudal aspect. A torque screw 22 is provided for securing hooks; and further a bead 23 (FIG. 2E) is provided for securing to the upper cephalad hook 21 stem. A spike 34 is provided to various embodiments assisting locking to the layered lamina surface 95. Optionally, it should be appreciated that spike 34 could be configured to any of hooks 21, 31, 59, 61 as further detailed herein. Additionally, a locking screw 42 is provided for tightening the vertical rods 41 as further detailed herein.

Figure 3B:
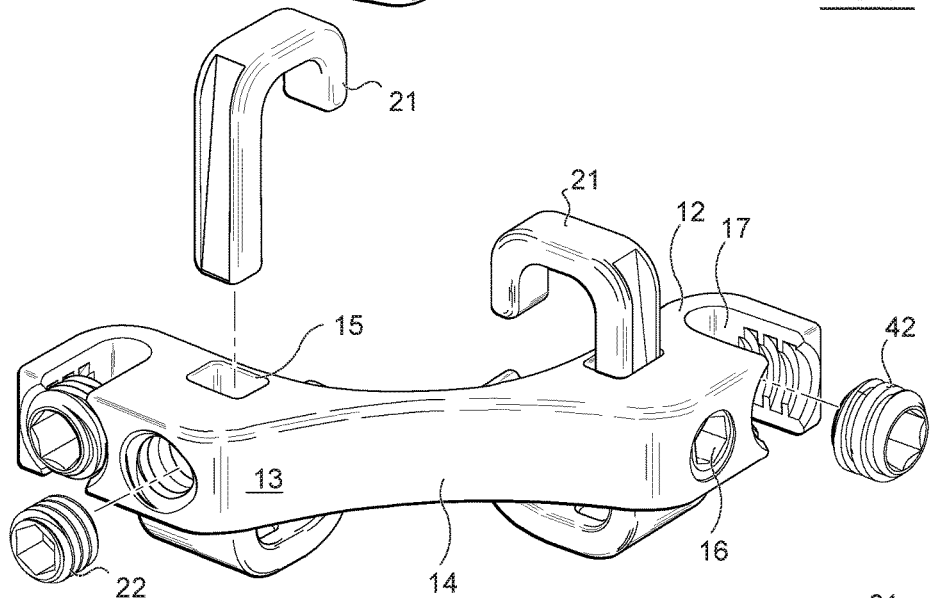
FIG. 3B is an additional exploded view of the first preferred device in the reverse position as compared to FIG. 3A.

Regarding FIG. 3B, an additional exploded view of the first preferred embodiment 10 is provided. A first threaded aperture 16 on a side of each base portion 12, 13 is used for tightening against a stem of the upper cephalad hook 21 via tightening screw 22. Also, each base portion 12, 13 has a U channel 17 (or slot 17) therethrough at a rear end thereof 12, 13 having threads along the sides of the U channel 17. The slot 17 is further rounded at the bottom of the U (in the top aspect) for receiving the vertical rods 41 for connecting at multiple levels 91, 92. Isthmus 14 comprises a thinner area 14 connecting wider masses 12, 13 form a composite base 11 and provides an approximate ninety degree offset to provide an offset angle with which to engage the lamina 95.

Figure 3C:
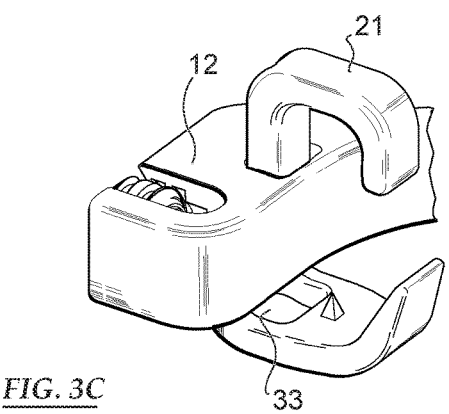
FIG. 3C is a perspective view of a singular base portion.

In its simplest form, the invention is a spinous laminar clamp base portion 12 (as shown in FIG. 3C) comprising a first base portion 12 providing structural integrity to the laminar clamp 10. As stated, a first aperture 15 is configured through a top and a bottom of the base portion 12 for slidingly receiving an upper cephalad hook 21. A lower jaw 31 is fixed to the base 12 opposite the cephalad hook 21, the cephalad hook 21 and the lower jaw 31 together clamp down on the laminar 95 surface.

In a preferred embodiment, the clamp assemblies 10, 11, 50, 51, 70 are made from surgical grade titanium, non-ferromagnetic material, for allowing imaging after implant. Or in various embodiments, components 11, 21, 31, 41, 51, 59, 61, 65 are made from biocompatible materials including titanium, plastic, steel, or composite material such as carbon fiber, graphene, or synthetic material. Also the titanium or alloy will be chosen to allow slight flexing at the vertical rods 41 to correct malalignment and frank subluxation. Malalignments are particularly deformities cause by injury, posture or genetics, for example. Similarly, the clamps upper 21, 59 and lower 31, 61 jaws allow for slight flexing to adjust to various shapes of the lamina 95.

Figure 4A:
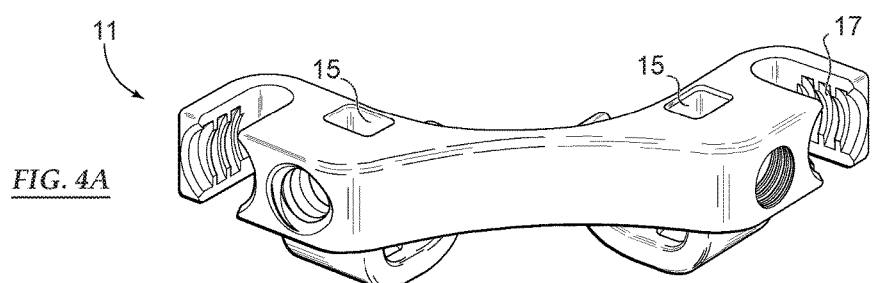
FIG. 4A is a rear isometric view of the preferred device with the cephalad hooks removed revealing their apertures.
Figure 4B:
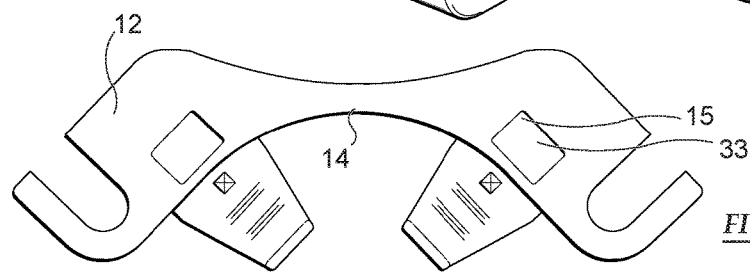
FIG. 4B is a top plan view thereof.
Figure 4C:
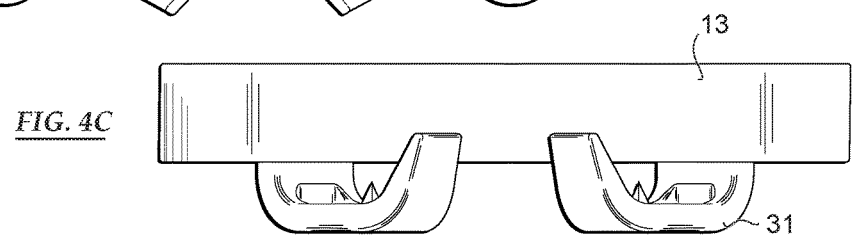
FIG. 4C is an elevational view thereof.
Figure 4D:
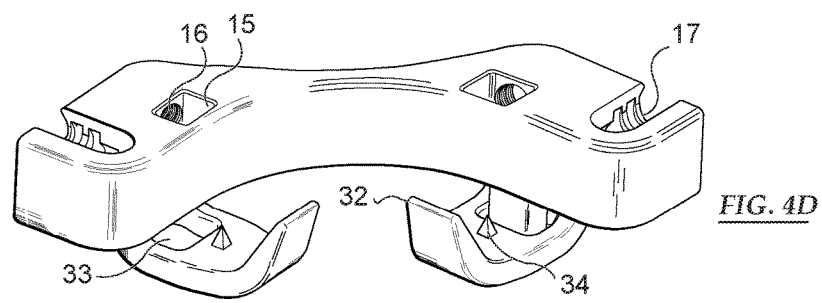
FIG. 4D is a forward isometric view of same.
Figure 4E:
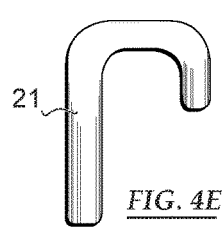
FIG. 4E, FIG. 4F and FIG. 4G illustrate various views of a cephalad hook configured to the present invention.
Figure 4F:
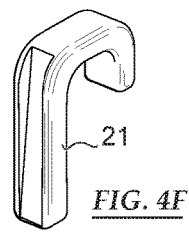
Figure 4G:
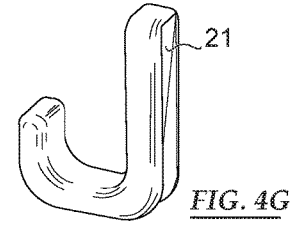

FIG. 4A through 4D provide various views of a pair of clamps connected by the center isthmus 14 with the cephalad hooks 21 removed revealing their apertures 15. As best shown in FIG. 4D, the fixed lower jaw 31 of each base portion 12, 13 has an aperture 33 therethrough for receiving the cephalad hook 21 as it is tightened and clamped. The lower jaw 31 further has a spike 34 configured thereto. FIG. 4E, FIG. 4F and FIG. 4G illustrate various view of a cephalad hook 21 configured having a stem portion and a hook portion, the hook portion in the form of a "J" as shown.

Figure 5A:
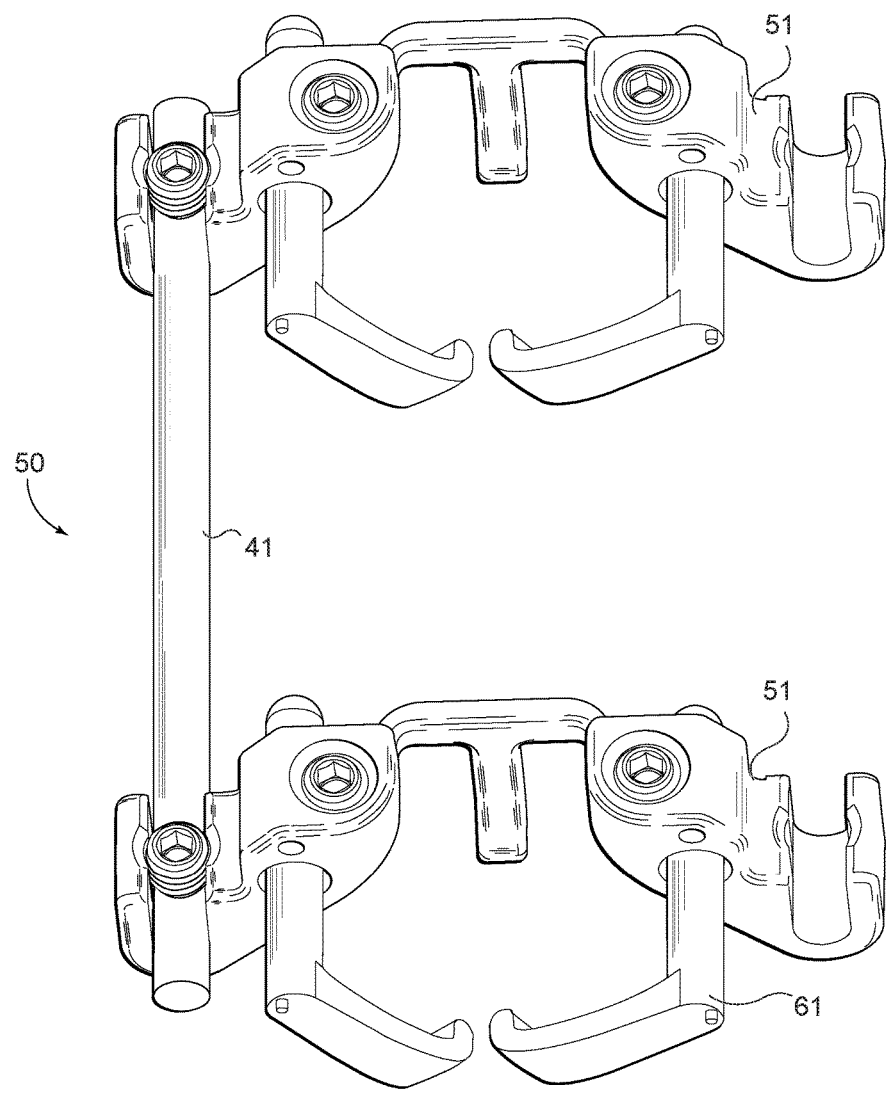
FIG. 5A is a perspective view of yet a second preferred embodiment of the present invention with a unique combination of fixed and/or adjustable hooks however comparable to the first preferred embodiment.
Figure 5B:
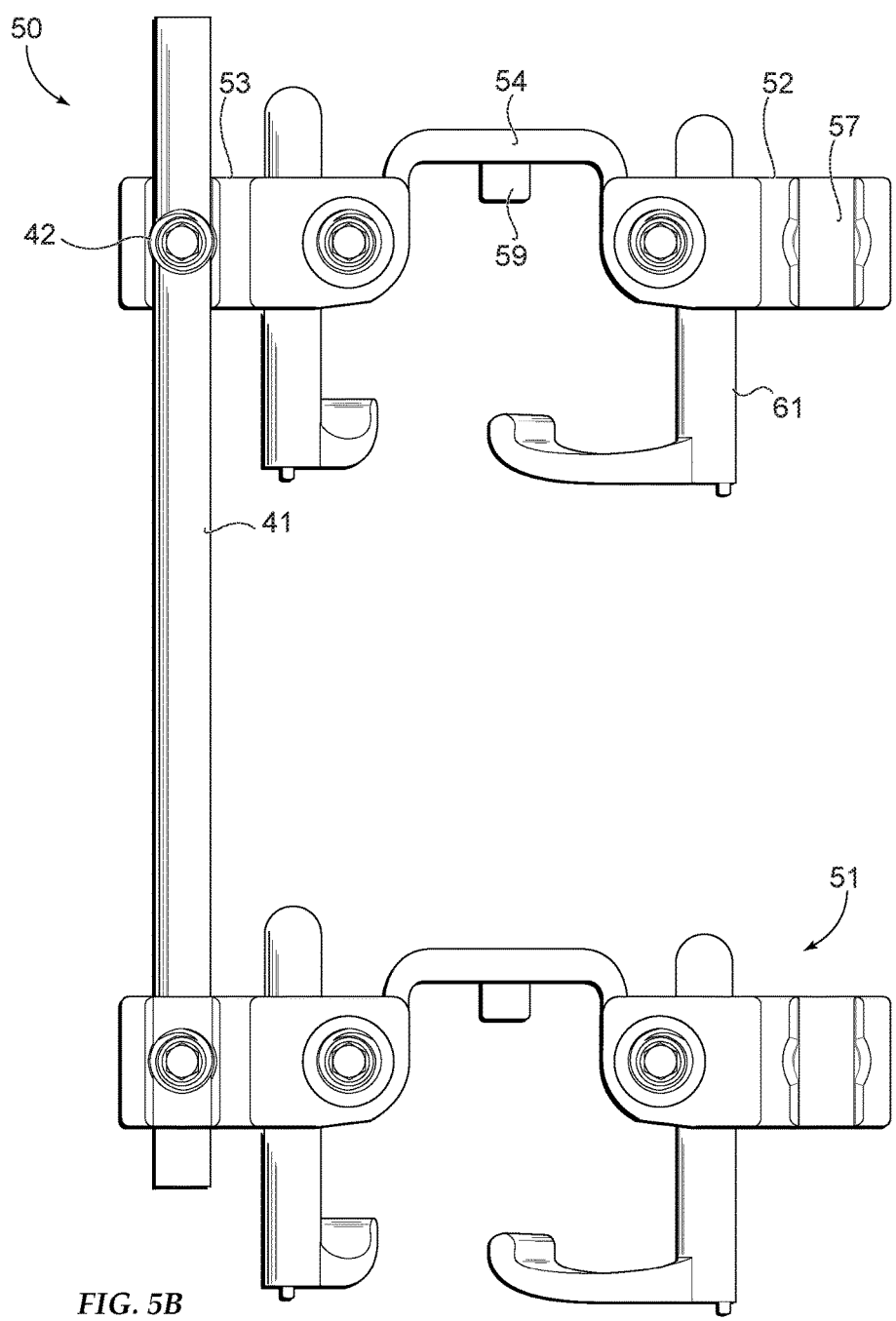
FIG. 5B is an elevational view of the second embodiment in a preferred position.

With regard to FIG. 5A and FIG. 5B, a second preferred embodiment 50 is illustrated in an isometric view and an elevational view, respectively. Herein each 50, 10 may be referred to as three and four-point fixation, respectively. Also, an aggregate of embodiments 10, 50, 70 include multiple options for combining fixed and adjustable hooks 21, 31, 59, 61 for each embodiment 10, 50. It should be appreciate that various embodiments 10, 50, 70 herein may in fact be inverted, so the cephalad and caudal aspect may be flipped upside down. This may also depend on the amount of disruption of the cephalad laminar 95 or any of various pathologies. In another useful example, a type "Jefferson's Fracture," wherein a patient suffers a ring fracture of the cervical one (C1) vertebra 91, a two pronged hook 21 may be provided on the cephalad aspect to secure around the fracture site to immobilize the ring allowing fusion and simultaneously securing to the subjacent 92 vertebra (C2). This slight variation provides better fixation.

Figure 5C:
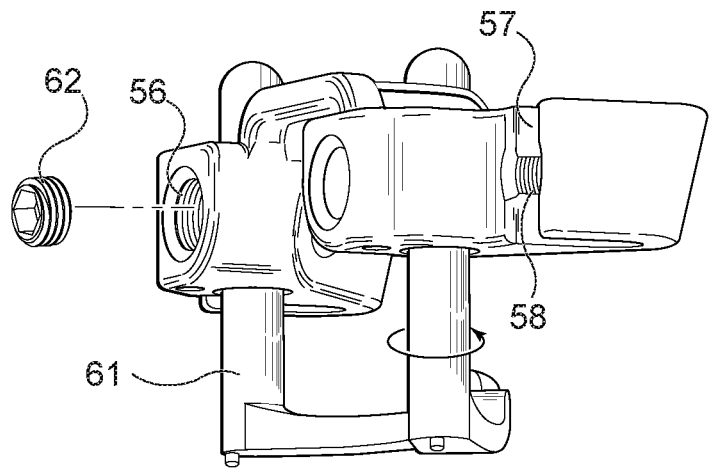
FIG. 5C is an isometric view of a single vertebral level of the second preferred clamp assembly from a side vantage point.
Figure 5D:
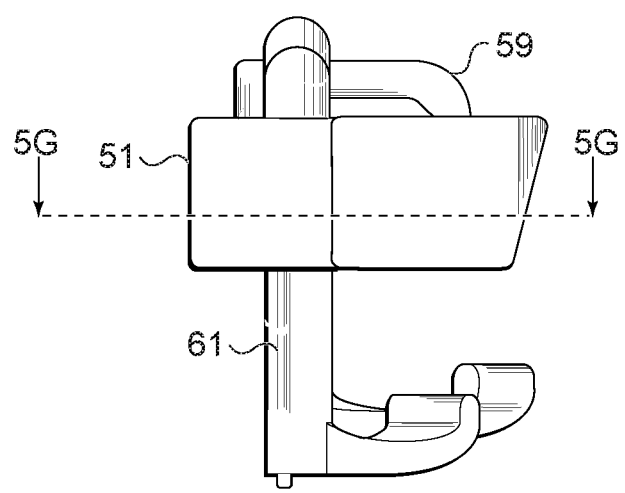
FIG. 5D is a profile view thereof.
Figure 5E:
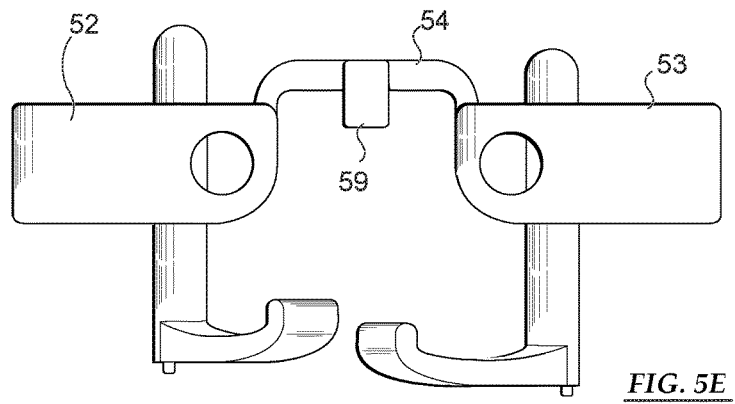
FIG. 5E is an elevational view thereof.

Still with regard to FIG. 5B, and also with regard to FIG. 5C, FIG. 5D, FIG. 5E and FIG. 5F, the illustrated invention is a spinous laminar clamp 50 for fixating and unitizing a human spine 99 comprising: a first base portion 52, and a first aperture 55 through a top and a bottom of the first base portion 52 for receiving a first lower caudal hook 61. FIG. 5E particularly illustrates where the first lower caudal hook 61 is adjustable vertically via the first aperture 55. In other words, it 61 is able to slide up and down, for vertical adjustment. As before, the two base portions 52, 53 at the same vertebral level 51 form a collective base 51 connected by a bridge 54, or isthmus.

Additionally, the lower caudal hook 61 can rotate (FIG. 5C) about its vertical axis, or its stem, for optimally engaging a laminar surface 95 that may vary in size or orientation because of its inherent complex geometry. The cylindrical shape of the hook 61 stem and its aperture 55 provide for the rotation.

Regarding FIG. 5A and FIG. 5B, a single upper cephalad hook 59 is configured to the first base portion 52, broadly and generally speaking. However, the cephalad hook 59 is more specifically configured to the first base portion 52 and the second base portion 53 via a bridge 54 connecting the first 52 and second 53 base portions, at a center thereof 54. Still more specifically, the bridge 54 has an arm that extends forward (FIG. 5D, for example, arm extends forward with a hook 59 at an end thereof). The arm and hook 59 together with hooks 61 are provided for tightening and clamping to either side of a vertebral surface at a desired level, for example the (C2) 92. In this example 51, first and second caudal hooks 61 together with the first cephalad hook 59 provide a three-point fixation to the spine, the three-point fixation being particular to a single vertebral level. Still further, spike 34 can be configured to cephalad hook 59, or caudal hooks 61, as desired by the particular application.

Figure 5F:
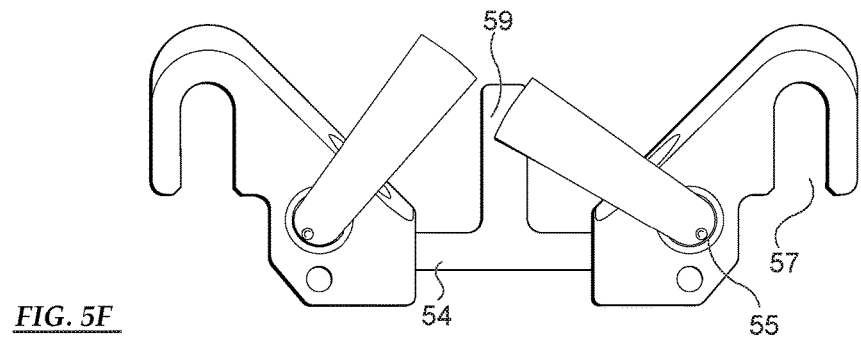
FIG. 5F is a top plan view of the second preferred device.
Figure 5G:
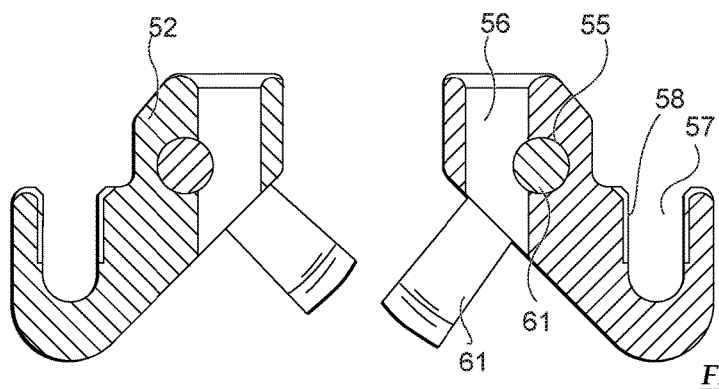
FIG. 5G is a cross-sectional view of the second preferred embodiment taken along sectional line 5G-5G in FIG. 5D.

Particularly with regard to FIG. 5C, FIG. 5F, and cross sectional view FIG. 5G, aperture 55, aligned vertically, connects to a threaded aperture 56 aligned horizontally through a rear of first 51 and second 52 base portions. FIG. 5G specifically illustrates how a side of vertical aperture 55 connects to a side of horizontal aperture 56. Tightening screw 62 is provided to secure the hook 61 stem vertically and rotationally. Different than other embodiments 10, 70, tightening screw 62 will secure to a side of the screw against hook 61; hence contact bead 23 will not be applicable to this example 50.

An additional embodiment 70 is illustrated in FIG. 6A through FIG. 6C. In this example horizontal aperture 56 is replaced with the slot 76 as in previous embodiments 10, 50 having slots 17, 57 for connecting rods 41. Hence, the invention in this aspect 70 comprises a first slot 76 through the top and the bottom of the first base portion 52 further comprising an opening to a rear of the first base portion 52 (the opening providing a "U" channel in the top aspect (FIG. 6C, for example, or FIG. 4A and FIG. 4B, U channel 17), the opening configured to slidingly receive a stem of the first lower caudal hook 61 in its upright position. In this configuration, the caudal hook 61 may be inserted from the rear instead of up from underneath as with aperture 55. Hence, hook 61 can be attached inferiorly or caudally without having to insert from underneath. It is additionally contemplated herein, that hook 61 may be attached inferiorly by being dropped down from above through slot 76 if the hooking portion of hook 61 were made small enough to fit through slot 76.

Threads are configured to the slot 76 and are just like slots 17, 57, to receive a tightening screw 62 through the rear of the first base portion 51 (and similarly second base portion 52) for contacting the stem of the first lower caudal hook 61. Similar to previous embodiments 10, 50 the threads 58 are further configured partially hemispherically through opposing walls of the first slot 76.

Also with regard to embodiments 50, 70, FIG. 5A through FIG. 6C, a third slot 57 through a top and a bottom of the first base portion 52 is for receiving a first connecting rod 41. The third slot 57 is positioned at an outer portion of the first base portion 52 with respect to the first slot 76, or first aperture 55. The first connecting rod 41 is configured to a third base portion (for example third base portion is one half of collective base portion 51 at the lower level in FIG. 5B). The third base portion further provides fixation at a vertebral level directly above or below a vertebral level of the first and second base portion 52, 53, (also termed collective base portions 51); and thereby providing fixation at two vertebral levels. Regarding third embodiment 70, FIG. 6C, contact bead 23 may be added to tightening screw 62 for optimally contacting to hook 61 stem. Also in this embodiment 70, a hook with shorter 65 or longer 61 vertical stems are provided depending on the application.

With all embodiments 10, 50, 70 and combinations thereof, it shall be appreciated that the invention can easily fixate all cervical levels minimizing risk to neutral and vascular structures and can be accomplished with direct visualization and without a need for specific radiographic imaging. Device imaging can be facilitated with markings on the device if it is not metal. If it is metal, it can be clearly seen. The clamp assemblies 10, 50, 70 as they sit, do not require any drilling into the bone laterally near the vertebral arteries or near any nerve roots or near the spinal canal as it sits posteriorly on the lamina 95 away from neutral components. It 10, 50 70 requires smaller incisions and the insertion device retreats directly out of the wound and can be angled off to the side as to be held out of the field of view. There is symmetry in the vertebral units 11, 51 and hooks 21, 31, 59, 61 on left/right and caudal/cephalad in either a three-point or four-point assemblies 10, 50, 70 depending on pathology. Still further, each embodiment 10, 50, 70 provides ability to be bent and/or shaped by bending a component so it fits more proximally to the bone 99 without taking up superfluous space.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed above even when not initially claimed in such combinations.

While the particular Spinous Laminar Clamp Assembly herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

What is claimed is:

1. A spinous laminar clamp for fixating and unitizing a human spine comprising:
   a first base portion providing structural integrity thereto;
   a first slot through a top and a bottom of the first base portion for receiving a first lower caudal hook, wherein the first lower caudal hook is slidingly adjustable vertically via the first slot; and
   an upper cephalad hook configured to the first base portion, the upper cephalad hook and the lower caudal hook together for tightening to a vertebral surface for fixating and unitizing the human spine.

2. The spinous laminar clamp for fixating and unitizing vertebrae of claim 1, wherein the first slot through the top and the bottom of the first base portion further comprises an opening to a rear of the first base portion, the opening providing a "U" channel in the top aspect, the opening configured to slidingly receive a stem of the first lower caudal hook in its upright position thereby providing for a rear loading of the first caudal hook, further thereby the stem of the first lower caudal hook is able to slide laterally in its upright position for surgical placement and subsequently can slide up and down in its upright position via the first slot, the opening further comprising threads, the threads configured to receive a tightening screw through the rear of the first base portion for contacting the stem of the first lower caudal hook, the threads further configured partially hemispherically through opposing walls of the first slot.

3. The spinous laminar clamp for fixating and unitizing vertebrae of claim 2, the tightening screw comprising a bead at an end thereof for optimally contacting and securing the stem of the first lower caudal hook.

4. The spinous laminar clamp for fixating and unitizing vertebrae of claim 1, wherein the first lower caudal hook comprises a stem, the stem being cylindrical in shape, the cylindrical shape providing rotation of the stem within the first slot, the rotation for aligning to a complex geometry of the vertebral surface.

5. The spinous laminar clamp for fixating and unitizing vertebrae of claim 1 further comprising:
   a second base portion in a common horizontal plane with said first base portion; and
   a second slot through a top and a bottom of the second base portion for receiving a second lower caudal hook, wherein the second lower caudal hook together with the first cephalad hook and first lower caudal hook for fixating and unitizing a human spine, wherein thereby the first and the second caudal hooks together with the first cephalad hook provide a three-point fixation to the spine, the three-point fixation being particular to a single vertebral level.

6. The spinous laminar clamp for fixating and unitizing vertebrae of claim 5, further comprising a bridge connecting the first base portion and the second base portion, the bridge being an isthmus between the first and the second base portions, wherein the bridge comprises said first cephalad hook at a center portion thereof, thereby the first cephalad hook is configured to the first base portion via said bridge, wherein the first and second base portions together form a first collective base on the common horizontal plane providing structural integrity to the spinous laminar clamp.

7. The spinous laminar clamp for fixating and unitizing vertebrae of claim 6, the first cephalad hook further comprising:
   an arm extending forward from the bridge, the arm having a curved portion at an end thereof; and
   a spike configured to the curved portion for fixedly contacting the vertebral surface.

8. The spinous laminar clamp for fixating and unitizing vertebrae of claim 5 further comprising:
   a third slot through a top and a bottom of the first base portion for receiving a first connecting rod, the third slot at an outer portion of the first base portion with respect to the first slot, wherein the first connecting rod is configured to a third base portion, the third base portion having fixation at a vertebral level directly above or below a vertebral level of the first and second base portion, thereby providing fixation at two vertebral levels.

9. A spinous laminar clamp comprising:
   a first base portion providing structural integrity thereto;
   a first aperture through a top and a bottom of the first base portion for slidingly receiving an upper cephalad hook; and
   a fixed lower jaw coupled to the first base portion opposite the cephalad hook, the cephalad hook and the lower jaw together for tightening to a vertebral surface.

10. The spinous laminar clamp of claim 9, wherein the fixed lower jaw comprises a hole therethrough to receive the cephalad hook stem, wherein the spinous laminar clamp further comprises a threaded aperture through a side of the first base portion configured with a tightening screw for tightening to the cephalad hook stem via the threaded aperture, further wherein the lower jaw comprises a spike for fixating and unitizing, further wherein the lower jaw and the cephalad hook together form an underbite thereby wherein the lower jaw protrudes slightly farther than the upper hook.

11. The spinous laminar clamp of claim 9, further comprising:
   a second base portion in a same horizontal plane with said first base portion;
   a second fixed lower jaw configured at an underside of the second base portion;
   a second aperture through a top and a bottom of the second base portion for receiving a second cephalad hook, wherein the second fixed lower jaw together with the first cephalad hook and first fixed lower jaw for fixating and unitizing a human spine, wherein thereby the first and second cephalad hook together with the first and second fixed lower jaw providing a four-point fixation to the spine, four-point fixation being particular to a single vertebral level; and
   an isthmus connecting the first and second base portion, the isthmus providing an approximately 90 degree offset with respect to the first and second base portions thereby providing said offset to the first and second cephalad hooks.

12. A spinous laminar clamp assembly providing fixation at multiple vertebral levels comprising:
   a first base portion configured to a first hook with a first stem slidingly received by the first base portion;
   a second base portion configured to a second hook with a second stem slidingly received by the second base portion, the second base portion in a first shared horizontal plane to the first base portion;
   a first isthmus between the first and the second base portion, the first isthmus having a third hook, wherein the first hook, second hook and third hook provide a three-point fixation to a first vertebral level;
   a third and a fourth base portion configured subjacent said first and said second base portions, the third and fourth base portion in a second horizontal plane further fixated to a second vertebral level; and a connecting rod coupling the first and second base portions to the third and the fourth base portions, the first, the second, the third and the fourth base portions together with the connecting rod providing fixation at the multiple vertebral levels.

13. The spinous laminar clamp assembly providing fixation at multiple vertebral levels of claim 12, further comprising an insertion instrument having an upper and a lower jaw at a distal end for grasping and tightening the first hook and the second hook to a vertebral surface.

14. The spinous laminar clamp assembly providing fixation at multiple vertebral levels of claim 12, the first, the second, the third, the fourth base portions each further comprising a slot through a top and a bottom, each slot being U-shaped in a top aspect wherein a pair of opposing side walls of the slot are threaded, forming a threaded side channel out of a rear of each of the first, the second, and the third base portions for tightening and securing the connecting rod being a vertical connecting rod for connecting the multiple levels.

* * * * *